US00PP27524P2

(12) United States Plant Patent
Hagiwara

(10) Patent No.: US PP27,524 P2
(45) Date of Patent: Jan. 3, 2017

(54) ***ILEX* PLANT NAMED 'SCREEN PLAY'**

(50) Latin Name: *Ilex integra×latifolia*
Varietal Denomination: Screen Play

(71) Applicant: Toshihiro Hagiwara, Saitama (JP)

(72) Inventor: Toshihiro Hagiwara, Saitama (JP)

(73) Assignee: ITSAUL PLANTS LLC, Alpharetta, GA (US)

( * ) Notice: Subject to any disclaimer, the term of this patent is extended or adjusted under 35 U.S.C. 154(b) by 100 days.

(21) Appl. No.: 14/545,138

(22) Filed: Mar. 30, 2015

(51) Int. Cl.
*A01H 5/00* (2006.01)

(52) U.S. Cl.
USPC ..... Plt./247

(58) Field of Classification Search
USPC ..... Plt./226, 247
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Ilex* plant named 'Screen Play', that is characterized by its well-branched, dense, upright plant habit with suitablity for use as a hedge or privacy screen, its vigourous growth habit with plants growing an average of 1.5 m per year in Georgia when young, its large leaves that emerge light green tinged with bronze in color and maturing to a deep green color, its leaves that are glossy and spineless with very finely serrated margins, its berries that ripen to a deep red color in early fall and persist on the plant through the winter, its cold tolerance; remaining evergreen in U.S.D.A Zone 7, and its ease of pollination by ambient pollen when grown in Georgia.

2 Drawing Sheets

Botanical classification: *Ilex integra×latifolia.*
Cultivar designation: 'Screen Play'.

BACKGROUND OF THE INVENTION

The present invention relates to a new and distinct cultivar of *Ilex integra×latifolia* and will be referred to hereafter by its cultivar name, 'Screen Play'. 'Screen Play' represents a new spine-free (consumer friendly) evergreen holly which displays attractive red fruit all winter and is used as a landscape specimen or hedge.

The Inventor discovered the new cultivar, 'Screen Play' in 1994 as a naturally occurring branch mutation of an unnamed and unpatented plant of *Ilex integra×latifolia* from the Inventor's breeding program that was growing in a trial bed in Saitama City, Japan. The new cultivar was discovered on a plant that was among numerous *Ilex integra×latifolia* seedings that originated from the Inventor's breeding program in 1987.

Asexual propagation of the new cultivar was first accomplished by the Inventor using semi-soft wood cuttings in Saitama City, Japan in 1994. Subsequent asexual propagation by semi-soft wood cuttings from 2004 to 2009 has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Screen Play' as a new and distinct cultivar of *Ilex*.

1. 'Screen Play' exhibits a well-branched, dense, and upright plant habit and is suitable for use as a hedge or privacy screen.

2. 'Screen Play' exhibits a vigourous growth habit with plants growing an average of 1.5 m per year in Georgia when young.
3. 'Screen Play' exhibits large leaves that emerge light green tinged with bronze in color and mature to a deep green color.
4. 'Screen Play' exhibits leaves that are glossy and spineless with very finely serrated margins.
5. 'Screen Play' exhibits berries that ripen to a deep red color in early fall and persist on the plant through the winter.
6. 'Screen Play' exhibits cold tolerance; remaining evergreen in U.S.D.A Zone 7.
7. 'Screen Play' is readily pollinated by ambient pollen in Georgia.

The parent of 'Screen Play', differs from 'Screen Play' in having leaves that are smaller in size and lighter in color, and in having a less dense plant habit. 'Screen Play' can most be most closely compared to the *Ilex* hybrid cultivars 'Emily Bruner' (not patented) and 'Nellie Stevens' (not patented). 'Emily Bruner' is similar to 'Screen Play' in having a dense, evergreen plant habit and in producing red berries that persist through the winter. 'Emily Bruner' differs from 'Screen Play' in having a leaves with spiney margins, in having larger more conspicuous flowers, and in having a broader plant habit. 'Nellie Stevens' is similar to 'Screen Play' in producing red berries that persist though the winter and in having a large plant habit that is suitable for use as a privacy screen. 'Nellie Stevens' differs from 'Screen Play' in having leaves that are lighter green in color, recurved and have thorns, in having a more rounded plant habit, in having a less vigorous growth habit, and in being known to self-pollinate.

BRIEF DESCRIPTION OF THE DRAWINGS

The accompanying colored photographs illustrate the overall appearance and distinct characteristics of the new

*Ilex*. The photographs were taken of 4.5 year-old plants of 'Screen Play' as grown outdoors in 15-gallon containers in Alpharetta, Ga.

Figure 1:
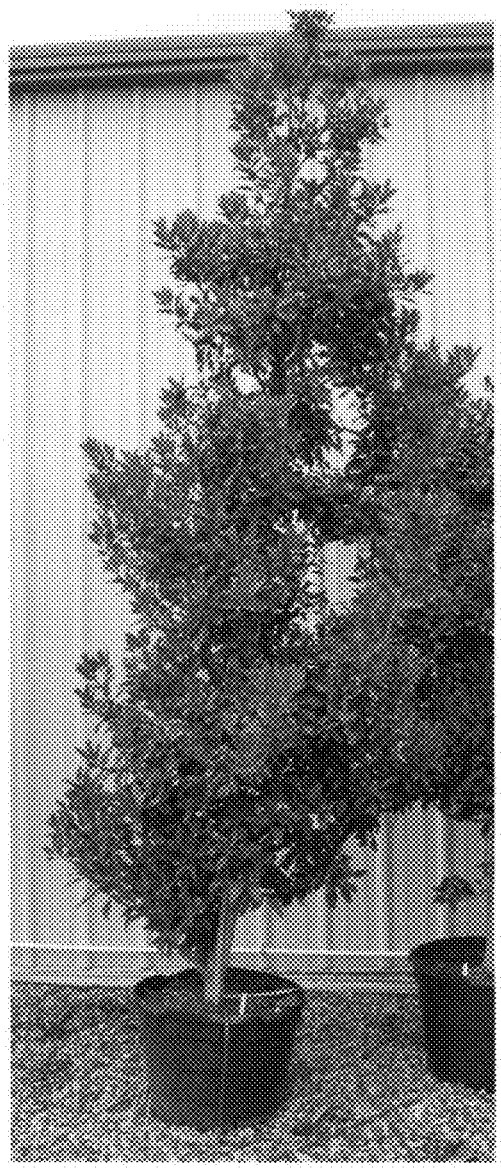

The photograph in FIG. 1 provides a side-view of 'Screen Play'.

Figure 2:
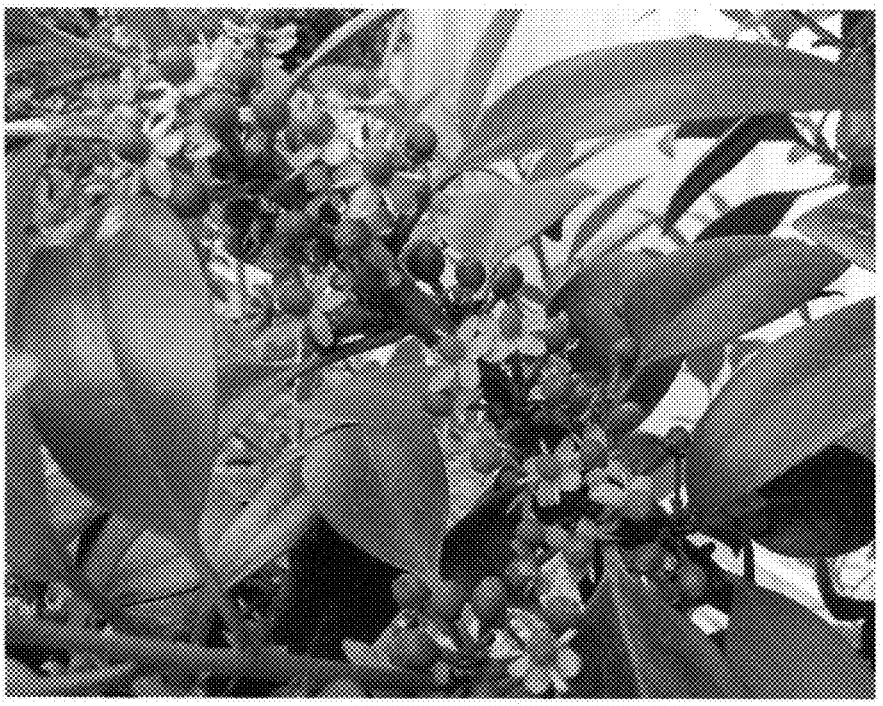

The photograph in FIG. 2 provides a close-up view of the flowers of 'Screen Play'.

Figure 3:
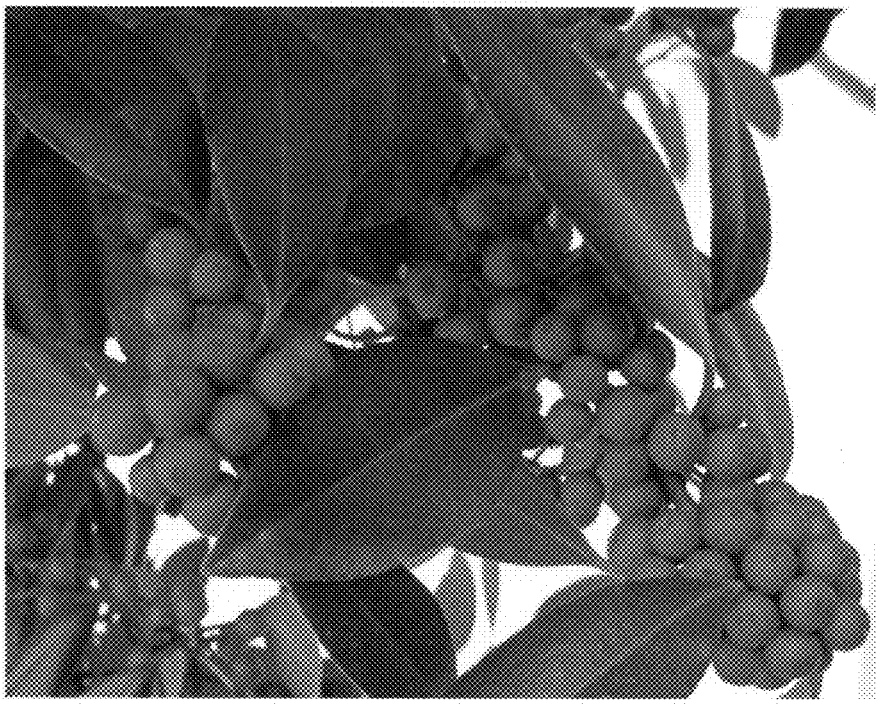

The photograph in FIG. 3 provides a close-up view of the fruit of 'Screen Play'. The colors in the photographs are as close as possible with the digital photography techniques available, the color values cited in the detailed botanical description accurately describe the colors of the new *Ilex*.

DETAILED BOTANICAL DESCRIPTION OF THE PLANT

The following is a detailed description of 4 year-old plants of the new cultivar as grown outdoors in 15-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Spring in Alpharetta, Ga.

*Plant type*.—Evergreen tree (in U.S.D.A. Zone 7 or above).

*Plant habit*.—Upright, densely branched with dense foliage.

*Height and spread*.—Reaches 7 to 9 m in height and 3.6 to 4.6 m in spread after 10 years in the ground in Japan and Georgia.

*Cold hardiness*.—At least to U.S.D.A. Zone 7; soft new growth is susceptible to early winter freeze damage, as such plants should not be fertilized in Fall.

*Diseases and pests*.—No particular susceptibility and resistance to diseases or pests as has been observed.

*Root description*.—Medium thickness, near 155D in color.

*Growth rate*.—Initially vigourous; average of 1.5 m per year when young, slows with maturity.

*Propagation*.—Semi-soft wood cuttings.

*Root development*.—Roots initiate in as little as three weeks in late winter with bottom heat at 23 to 27° C.; root initiation can be variable, up to 16 weeks depending on conditions; rooting is facilitated by removal of all foliage/petioles from the cuttings, once a root reaches 3 cm in length, rooting is vigorous and will fully develop in a 9-cm pot in about 4 weeks.

Branch description:

*Branch shape*.—Round.

*Branch color*.—New growth; 144A to 144B, mature branches; underlay 146A, overlay of bark a blend of 199A and 199B, oldest bark; 199B and 199C with some streaks of 146A.

*Stem size*.—Main stem; an average of 2.1 m in length and 5.5 cm in width measured at soil level, 3 cm in width at mid point, and 5 to 7 mm in width at apex, primary lateral branches; 3 cm in width and slightly shorter than main stem, secondary lateral branches; average of 1.3 m in length near plant base and 0.7 m in length at half the plant height, lateral fruiting branches; ranges from 15 to 35 cm in length and 3 to 8 mm in width.

*Stem surface*.—New growth; glossy, smooth with a rubber texture, mature surface; relatively smooth and slightly glaucous, mature bark; finely barked and dull.

*Internode length*.—Up to 4 cm in length.

*Branching*.—Primary lateral branches; average of 2 from near base of main stem, held at 35° relative to vertical, secondary lateral branches; average of 11 per main stem or primary branch, held at 45° angle, fruiting branches; up to 20 all along secondary laterals at two weeks after bloom initiation.

*Stem strength*.—Very strong.

Foliage description:

*Leaf shape*.—Elliptic to oblong.

*Leaf division*.—Simple.

*Leaf base*.—Cuneate.

*Leaf apex*.—Acute to acuminate.

*Leaf venation*.—Pinnate, not conspicuous, color matches leaf coloration.

*Leaf margins*.—Very finely serrated, spineless.

*Leaf attachment*.—Petiolate.

*Leaf arrangement*.—Alternate.

*Leaf aspect*.—Young foliage held at a 20° angle to vertical stem, mature foliage held at a 50° angle to vertical stem.

*Foliage fragrance*.—None.

*Leaf surface*.—Young upper surface; very glossy and smooth with a rubber texture, young lower surface; satiny and smooth, mature upper surface; very glossy and sturdy, mature lower surface; matte and smooth.

*Leaf color*.—Young upper surface; and color between 146A and 137B and tinged with 174A, young lower surface; 146D and tinged with 174A, mature upper surface; N137A, mature lower surface; 146B.

*Leaf size*.—Average of 9 cm in length and 3.5 cm in width.

*Leaf quantity*.—Up to 13 per mature lateral branch 20 cm in length, up to 20 per young lateral branch 45 cm in length.

*Petioles*.—An average of 2.5 cm in length and 2 mm in width, 146D in color, glabrous surface.

*Leaf buds*.—Up to 3 mm in length and diameter, outside scales; N200A in color, flaky and dull on both surfaces, inner portion; 143C in color with a glabrous surface.

*Stipules*.—About 1 mm in diameter and 165B in color.

Flower description:

*Inflorescence type*.—Clusters of female flowers at axils of lateral branches.

*Inflorescence*.—Tightly packed cluster of flowers, an average of 3 cm in width and 2 to 3 cm in length so that adjacent clusters nearly touch.

*Lastingness of flowers*.—About 8 days.

*Flower size*.—Average of 6 mm in height and 1 cm in diameter.

*Flower fragrance*.—None.

*Flower number*.—An average of 12 flowers per cluster and an average of 8 clusters per lateral branch.

*Flower aspect*.—Upright to outward.

*Flower buds*.—Globose in shape, an average of 4 mm in length and 3.5 mm in width, 145C in color.

*Corolla features*.—Petals are unfused and arranged in a rotate form, slightly cupped.

*Petals*.—4, elliptic to oblong in shape, glabrous and waxy on upper and lower surface, entire margins, round apex, truncate base, an average of 5.5 mm in length and 4.5 mm in width

*Calyx*.—Inconspicuous, spreading, un fused sepals.

*Sepal*.—4, ovate in shape, entire margin, an average of 2 mm in length and width, acture apex, truncate base, waxy on upper and lower surface, 139C on upper and lower surface.

*Peduncle*.—Round in shape, an average of 0.5 cm in length and 1 mm in diameter, waxy surface, 139C in color.

*Pedicel*.—None, peduncles attached to branch.

Reproductive organs:

*Gynoecium*.—1 pistil, 4-carpelled, globose in shape, 6 mm in length and 4 mm in width, 137D in color.

*Androcoecium*.—4 stamens, sterile, 3 mm in length and 0.7 mm in width, anthers are 0.8 mm in length and width, conical in shape, not fertile, no pollen is produced (female plants).

*Fruit/seeds*.—Fruit; a drupe, round in shape, an average of 7 mm in height and diameter, satiny surface, matures to 45A in color, seed; 4, an averge of 6 mm in length and 2 mm in width, oblong in shape with a flattened side, 160B in color, an average of 10 berries per flowering leaf axil.

It is claimed:

1. A new and distinct cultivar of *Ilex* plant named 'Screen Play' as herein illustrated and described.

* * * * *